United States Patent [19]
McLaughlin et al.

[11] Patent Number: 5,955,497
[45] Date of Patent: Sep. 21, 1999

[54] BIOACTIVE ACETOGENINS

[75] Inventors: Jerry L. McLaughlin; David C. Hopp, both of West Lafayette, Ind.

[73] Assignee: Purdue Research Foundation, West Lafayette, Ind.

[21] Appl. No.: 09/028,558

[22] Filed: Feb. 24, 1998

Related U.S. Application Data

[60] Provisional application No. 60/039,001, Feb. 25, 1997.
[51] Int. Cl.$^6$ ...................... A61K 31/365; C07D 307/58
[52] U.S. Cl. ............................................. 514/473; 549/320
[58] Field of Search ............................... 549/320; 514/473

[56] References Cited

U.S. PATENT DOCUMENTS

| | | | |
|---|---|---|---|
| 4,721,727 | 1/1988 | Mikolajczak et al. | 514/473 |
| 4,855,319 | 8/1989 | Mikolajczak et al. | 514/473 |
| 5,229,419 | 7/1993 | McLaughlin et al. | 514/473 |
| 5,536,848 | 7/1996 | McLaughlin et al. | 549/320 |

OTHER PUBLICATIONS

Gu, Zhe–ming et al., "New Cytotoxic Annonaceous Acetogenins: Bullatanocin and cis– trans–Bullatanocinone From Annona Bullata (Annonaceae)", 1993, *Tetrahedron*, vol. 49, p. 747.

Gu, Zhe–ming et al., "Bullacin: A New Cytotoxic Annonaceous Acetongenin From Annona Bullata", 1993, *Heterocycles*, vol. 36, No. 10, pp. 2221–2228.

Gu, Zhe–ming et al., "30–, 31–, and 32–Hydroxybullatacinones: Bioactive Terminally Hydroxylated Annonaceous Acetogenins from Annona Bullata", Jun. 1993, *Journal of Natural Products*, vol. 56, No. 6, pp. 870–876.

Rupprecht, J. Kent et al., "Annonaceous Acetogenins: A Review", Mar.–Apr. 1990, *Journal of Natural Products*, vol. 53, No. 2, pp. 237–278.

Fang, Xin–ping et al., "Annonaceous Acetogins: An Updated Review and Appendices", 1993, *Phytochemical Analysis*, vol. 4, pp. 27–67.

Fang, Xin–ping et al., "A New Type of Cytotoxic Annonaceous Acetogenin: Giganin from Goniothalamus Giganteus", 1993, *Bioorganic & Medicinal Chem. Letters*, vol. 3, No. 6, pp. 1153–1156.

Hopp et. al., J. of Natural Products, 59(2), pp. 97–99, Feb. 1996.

Advance ACS Abstracts, vol. 4, No. 2 (Abstract of Hopp et. al., J. of Natural Products, 59(2), pp. 97–99, Feb. 1996), Jan. 15, 1996.

Ratnayake et al, Can. J. Chem., 72, pp. 287–293, 1994.

*Primary Examiner*—Bernard Dentz
*Attorney, Agent, or Firm*—Barnes & Thornburg

[57] ABSTRACT

Novel acetogenins isolated from *Annona squamosa* of the family Annonaceae are described. The substantially pure acetogenins of the invention exhibit cytotoxicity to human tumor cell lines as well as selective cytotoxicity for various human tumor cell lines.

6 Claims, No Drawings

BIOACTIVE ACETOGENINS

This application claims priority under 35 U.S.C. 119 (e) (1) based on verified Provisional application 60/039,001 filed Feb. 25, 1997.

FIELD OF INVENTION

This invention relates to the isolation, identification and use of natural products as anti-tumor agents. More particularly this invention is directed to substantially pure forms of cytotoxic Annonaceous acetogenins, squamotacin and molvizarin, and their use in treating patients having tumors.

BACKGROUND AND SUMMARY OF THE INVENTION

In recent years, an increased interest in the phytochemistry of the Annonaceae has been sparked by the bioactivity-directed isolation of the antileukemic Annonaceous acetogenin, uvaricin, from *Uvaria acuminata*. Acetogenins are $C_{35}-C_{39}$ compounds and typically contain two long hydrocarbon chains, one of which connects a terminal 2,4-disubstituted-γ-lactone to a variable number of tetrahydrofuran (THF) rings. The hydrocarbon chains contain a number of oxygenated moieties which can be hydroxyls, acetoxyls and/or ketones.

All acetogenins found to date contain multiple stereocentres, the elucidation of which often presents daunting stereochemical problems. Because of their waxy nature, the acetogenins do not produce crystals suitable for X-ray crystallographic analysis. Relative stereochemistries of ring junctions have typically been determined by comparison of natural compounds with synthetic model compounds and such methods have proven to be invaluable with the acetogenins. Recently, the absolute stereochemistries of the carbinol centers of acetogenins have been determined with the help of synthetic model compounds and high field nuclear magnetic resonance (NMR) analysis of their methoxyfluoromethylphenylacetic acid (MPTA) esters (Mosher esters).

Most Annonaceous acetogenins are potently bioactive, but the mode of action of these compounds was unknown until Londerhausen et al. concluded in *Pesticide Science*, 33, 427–438 (1991), that they act to inhibit complex I of mitochondrial oxidative phosphorylation with an activity several times that of rotenone.

*Annona squamosa*, the custard apple, is a fruit tree, native to the new world and naturalized throughout the tropics. Research on the seeds of this plant has yielded 27 different acetogenins. By contrast, only four have been reported from the bark, and these are bullatacin, (3), 4-cis- and 2,4-trans-bullatacinones, and squamone. Through further work with the bark, each of these four known compounds have now been reisolated. Additional compounds have been isolated from this species, including asimicin, which is new to the bark of this species, molvizarin (2), which is new to the species, and squamotacin (1), which is a new acetogenin. The structure of squamotacin (1), molvizarin (2) and bullatacin (3) are shown below.

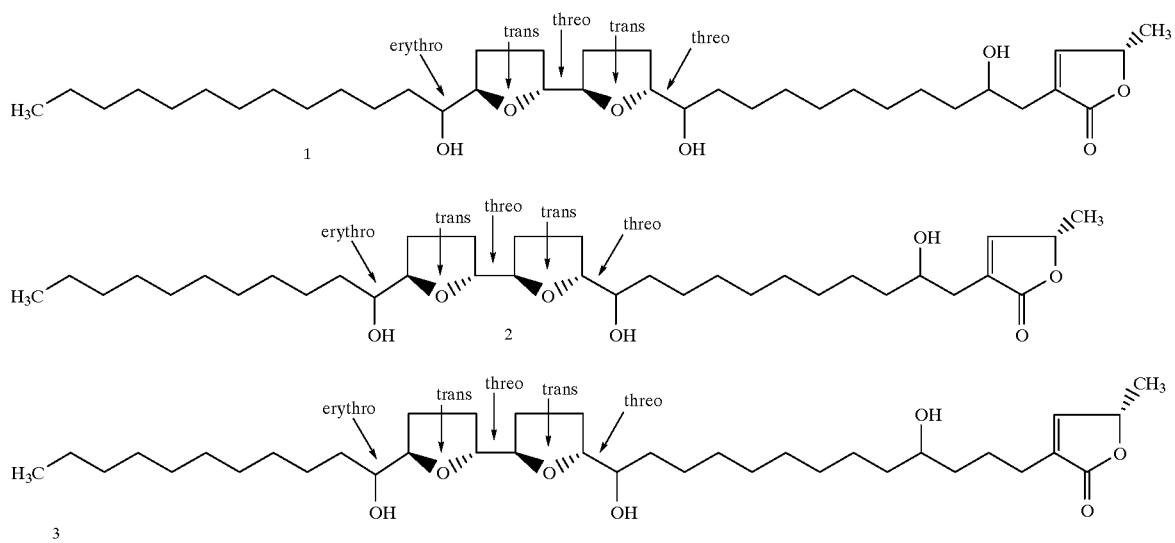

Molvizarin and squamotacin were isolated from *Annona squamosa* using column chromatography followed by HPLC. The active fractions containing these compounds were identified based on their bioactivity as revealed by the brine shrimp lethality test (BST), detailed in Example 2. Structure elucidation of the isolated compounds was carried out using NMR and MS analyses, the relative stereochemistry of squamotacin was suggested based on the close agreement with the NMR signals of bullatacin whose absolute stereochemistry is now known through Mosher ester analyses.

The present invention is directed to the isolation of two natural cytotoxic acetogenin compounds, squamotacin and molvizarin, and the preparation of chemotherapeutic compositions comprising those compounds for use in treating patients having tumors.

DETAILED DESCRIPTION OF THE INVENTION

Bullatacin is one of the most potent antitumor and pesticidal Annonaceous acetogenins currently known and was first reported and isolated from *Annona bullata* in 1989. The correct absolute configurations of the stereogenic carbinol centers of bullatacin were recently established by $^1$H- and $^{19}$F-NMR spectral analysis of bullatacin's (S)- and (R)-Mosher ester [methoxy (trifluoromethyl)phenylacetate or MTPA] derivatives. Bullatacin has shown potent in vivo antitumor activities, e.g., 67% tumor growth inhibition (TGI) at 50 μg/kg in athymic mice bearing A2780 human ovarian cancer xenografts. Bullatacin likely inhibits cancer cell growth through inhibition of mitochondrial electron transport systems to reduce the ATP levels. Over thirty Annonaceous acetogenins have been previously reported from the EtOH extract of the stem bark of *Asimina triloba*.

The present invention is directed to two Annonaceous acetogenins, squamotacin and molvizarin, isolated from *Annona squamosa* in substantially pure form. As used herein, the term substantially pure form is defined as greater than 95% pure. In one embodiment, Squamotacin and molvizarin are isolated in greater than 99% pure form. Applicants have discovered that those two compounds are cytotoxic to tumor cell lines, thus allowing their use for treating patients having a tumor.

One embodiment of the present invention provides pharmaceutical formulations comprising an effective amount of squamotacin or molvizarin for treating a patient having a tumor. As used herein, an effective amount of the acetogenin compound is defined as the amount of the compound which, upon administration to a patient, inhibits growth of tumor cells, kills malignant cells, reduces the volume or size of the tumors or eliminates the tumor entirely in the treated patient. Thus, the substantially pure compounds in accordance with this invention can be formulated into dosage forms using pharmaceutically acceptable carriers for oral or parenteral administration to patients in need of oncolytic therapy. In one embodiment, a chemotherapeutic composition comprises an anti-tumor effective amount of a compound selected from the group consisting of squamotacin and molvizarin and a pharmaceutically acceptable carrier therefor.

The effective amount to be administered to a patient is typically based on body surface area, patient weight, and patient condition. The interrelationship of dosages for animals and humans (based on milligrams per meter squared of body surface) is described by Freireich, E. J., et al., *Cancer Chemother. Rep.*, 50 (4): 219 (1966). Body surface area may be approximately determined from patient height and weight (see e.g., Scientific Tables, Geigy Pharmaceuticals, Ardley, N.Y., pages 537–538 (1970)). Preferred dose levels will also depend on the attending physicians' assessment of both the nature of the patient's particular cancerous condition and the overall physical condition of the patient. Effective anti-tumor doses of the present acetogenin compounds range from about 25 microgram per kilogram to about 800 micrograms per kilogram of patient body weight, more preferably between about 50 micrograms to about 400 micrograms per kilogram of patient body weight.

Effective doses will also vary, as recognized by those skilled in the art, dependant on route of administration, excipient usage and the possibility of co-usage with other therapeutic treatments including other anti-tumor agents, and radiation therapy.

The present pharmaceutical formulation may be administered via the parenteral route, including subcutaneously, intraperitoneally, intramuscularly and intravenously. Examples of parenteral dosage forms include aqueous solutions of the active agent, in an isotonic saline, 5% glucose or other well-known pharmaceutically acceptable liquid carrier. In one preferred aspect of the present embodiment, the acetogenin compound is dissolved in a saline solution containing 5% of dimethyl sulfoxide and 10% Cremphor EL (Sigma Chemical Company). Additional solubilizing agents such as cyclodextrins, which form specific, more soluble complexes with the present aetogenin compounds, or other solubilizing agents well-known to those familiar with the art, can be utilized as pharmaceutical excipients for delivery of the acetogenin compounds. Alternatively, the present compounds can be chemically modified to enhance water solubility.

The present compounds can also be formulated into dosage forms for other routes of administration utilizing well-known methods. The pharmaceutical compositions can be formulated, for example, in dosage forms for oral administration in a capsule, a gel seal or a tablet. Capsules may comprise any well-known pharmaceutically acceptable material such as gelatin or cellulose derivatives. Tablets may be formulated in accordance with conventional procedure by compressing mixtures of the active acetogenins and solid carriers, and lubricants well-known to those familiar with the art. Examples of solid carriers include starch, sugar, bentonite. The compounds of the present invention can also be administered in the form of a hard shell tablet or capsule containing, for example, lactose or mannitol as a binder, and conventional fillers and tableting agents.

The cytotoxicities of squamotacin, molvizarin and bullatacin were evaluated, in the same run, against a panel of six cell lines (Table 1). Adriamycin was included as a standard. The relative cytotoxicity of the compounds to non-tumor cells was determined based on the brine shrimp lethality assay (BSA). The panel of tumor cell lines tested includes human lung carcinoma (A-549), human breast carcinoma (MCF-7), human colon adenocarcinoma (HT-29), human renal carcinoma (A-498), human prostate adenocarcinoma (PC-3) and human pancreatic carcinoma (PACA-2).

TABLE 1

Bioactivities of squamotacin (1), molvizarin (2), bullatacin (3) and adriamycin (4).

| cpd # | BST (LC$_{30}$, g/mL) | cytotoxicity (ED$_{60}$, g/mL) | | | | | |
|---|---|---|---|---|---|---|---|
| | | A-549 | MCF-7 | HT-29 | A-498 | PC-3 | PACA-2 |
| 1 | 6.80 × 10$^{-3}$ | 2.77 × 10$^{-2}$ | >1 | 1.00 × 10$^{-3}$ | >1 | 1.72 × 10$^{-9}$ | 1.33 × 10$^{-4}$ |
| 2 | 5.26 × 10$^{-2}$ | 6.30 × 10$^{-2}$ | >1 | 7.32 × 10$^{-3}$ | 7.09 × 10$^{-1}$ | 4.47 × 10$^{-8}$ | 7.66 × 10$^{-3}$ |
| 3$^a$ | 1.59 × 10$^{-3}$ | 2.44 × 10$^{-6}$ | 6.96 × 10$^{-1}$ | >1 | 4.85 × 10$^{-5}$ | <10$^{-9}$ | <10$^{-9}$ |
| 4$^a$ | 2.57 × 10$^{-1}$ | 2.84 × 10$^{-2}$ | 3.47 × 10$^{-1}$ | 4.16 × 10$^{-2}$ | 2.49 × 10$^{-2}$ | 3.42 × 10$^{-1}$ | 3.17 × 10$^{-3}$ |

$^a$Brine Shrimp LC$_{50}$ taken from Can. J. Chem. Vol. 72, pages 287–293 (1994).

Each of the tested acetogenins were highly toxic to the brine shrimp larvae, and showed highly potent cytotoxicities against the tumor cell line Human prostate adenocarcinoma (PC-3). Due to the structural similarities between squamotacin and bullatacin, squamotacin was expected to show similar cytotoxicities to human tumor cells as those of bullatacin. Surprisingly, squamotacin showed less activity than bullatacin in five of the six cell lines tested, with HT-29 (colon) being the exception. However, squamotacin and molvizarin, unexpectedly, showed a high selectively for the prostate cell line (PC-3) (Table 1). In this cell line, squamotacin and molvizarin were over 100 million times as active as the positive control, adriamycin. Accordingly, it is anticipated that these compounds will be particularly effective as chemotherapeutic compounds for treating patients having prostate cancer.

Molvizarin (2) is nearly identical in structure to squamotacin, the only difference being that squamotacin has two additional methylene units on the hydrocarbon end. However, moivizarin does have the same spatial relationships between the terminal unsaturated γ lactone and the adjacent bis-THF rings. The spectra of cytotoxic selectivities of squamotacin and molvizarin were quite similar (Table 1). The fact that molvizarin (2) also showed selectivity for PC-3 strongly suggests that the distance between the γ lactone and the bis-THF ring system may be a critical factor influencing the activity of the acetogenins in certain cell types. The acetogenins are believed to exact their bioactive effects, at least in part, by inhibition of mitochondrial NADH ubiquinone oxidoreductase (complex I) and by inhibition of the ubiquinone-linked NADH oxidase that is peculiar to plasma membranes of cancerous cells. These effects deplete ATP levels and likely induce programmed cell death (apoptosis).

The surprising high selectivity of squamotacin and molvizarin for the PC-3 cell line indicates that these compounds will be effective anti-tumor agents for treating patients have prostate cancer. Accordingly, in one embodiment of the present invention an effective amount of a pharmaceutical formulation comprising squamotacin or molvizarin is utilized to treat patients suffering from prostate cancer. The pharmaceutical composition comprises an anti-tumor effective amount of a compound selected from the group consisting of squamotacin and molvizarin and a pharmaceutically acceptable carrier therefor. In accordance with another therapeutic regiment, the patient is administered both squamotacin and molvizarin, and those two compounds are administered either simultaneously or sequentially.

EXAMPLE 1
Preparation of Molvizarin and Squamotacin

Approximately 7.4 kg of *Annona squamosa* bark was collected and pulverized through a 2 mm screen in a Wiley mill. The pulverized bark was extracted by exhaustive percolation with 777 liters of 95% EtOH. Vacuum evaporation left a syrupy residue (F001). F001 was partitioned between $CHCl_3$—$H_2O$ (1:1), and the water solubles were freeze dried and labeled F002. The chloroform solubles were vacuum evaporated to form F003 and the insoluble interface was air dried and labeled F004. Then F003 was partitioned between hexane/90% aqueous MeOH (1:1). The 90% MeOH fraction was vacuum evaporated to a thick syrup and labeled F005 (545.5 g). From this, 500.5 g was added to an open column containing S1 gel (1.5 kg) and was developed using hexane with increasing amounts of chloroform followed by chloroform with increasing amounts of methanol. Bioactive fraction 24–29 appeared on TLC to contain acetogenins. These were combined (34.96 g) and treated with hexane and dichloromethane (2:1). The soluble portion (12.9 g $BSTLC_{50}$=0.0013) was added to an open column loaded with Si gel (220 g) and developed with hexane and increasing amounts of methanol.

Squamotacin (1) has been purified as a white powder (3.5 mg); $[\alpha]_D 2.59°$ (c=0.0027); IR ν max (KBr) 3450 (br, OH), 2924, 2853, 2358, 1750, 1456; 1073 cm$^{-1}$; UV γ max (MeOH), 207 nm (ε=7.9×10$^3$); HRFABMS (thioglycerol) m/z [MH$^+$] 623.4867 for $C_{37}H_{66}O_7$ (Calcd 623.4887); CIMS m/z 623 (31), 605 (100), 587 (69), 569 (28); EIMS m/z 387 (33) 335 (80), 317 (33) 283 (100); EIMS of TMSi derivative (see below for details); $^1$H-NMR (CDCl$_3$, 500 MHz), see Table 2; $^{13}$C-NMR (CDCl$_3$, 125 MHz), see Table 2.

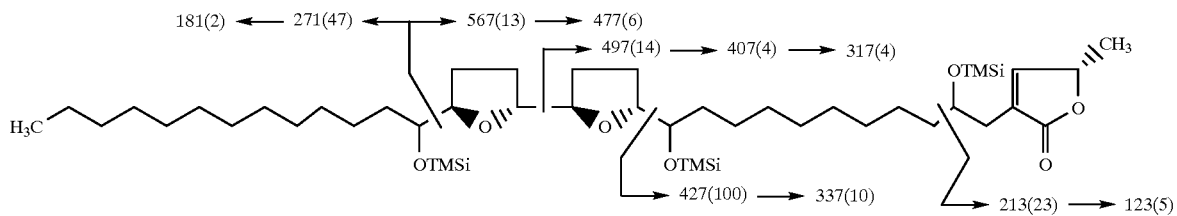

Molvizarin (2) was isolated from fraction (F005) of the ethanol extract using open columns, and then purified with repeated reversed-phase HPLC using MeOH and $H_2O$ (90:10, flow rate 10 mL/min) and normal phase HPLC using a solvent system of hexane-MeOH-THF (93:6:1, flow rate 10 mL/min). The respective $^1$H and $^{13}$C NMR signals at δ 3.37, 74.02, 3.84, 33.18, and 3.92, 82.44 (Table 2) indicated that two adjacent THF rings with flanking hydroxyls were present in the structure of 2 with a threo/trans/threo/trans/erythro relative configuration. Compound 2 was distinguished from 3 by the CIMS which showed a molecular ion with an m/z of 394, indicating that 2 contained only 35 carbons, while 3 has 37 carbons and a molecular weight of 622.

TABLE 2

$^1$H (500 MHZ, CDCl$_3$, J in Hz) and $^{13}$C NMR (125 MHZ, CDCl$_3$) Data of Molvizarin (2)

| no. | δ$_H$ | δ$_c$ | no. | δ$_H$ | δ$_c$ |
|---|---|---|---|---|---|
| 1 |  | 174.53 | 18 | 3.84 m | 82.71 |
| 2 |  | 131.00 | 19–20 | 1.96, 1.62 m | 28.30, 24.40 |
| 3a | 2.50 m | 33.12 | 21 | 3.92 m | 82.13 |
| 3b | 2.35 |  | 22 | 3.84 m | 71.26 |
| 4 | 3.84 m | 69.77 | 23 | 1.36 m | 32.29 |
| 5 | 1.46 m | 37.25 | 24 | 1.36 m | 25.47 |
| 6 | 1.36 m | 25.94 | 25–29 | 1.25 m | 29.50–29.21 |
| 7–10 | 1.25 m | 29.50–29.21 | 30 | 1.25 m | 31.76 |
| 11 | 1.36 m | 25.47 | 31 | 1.25 m | 22.55 |
| 12 | 1.36 m | 33.00 | 32 | 0.86 t (7.0) | 14.00 |
| 13 | 3.37 tt | 74.02 | 33 | 7.16 d (1.5) | 151.75 |
| 14 | 3.84 m | 83.18 | 34 | 5.04 d9 (1.5, 7.0) | 77.87 |

TABLE 2-continued $^1$H (500 MHZ, CDCl$_3$, J in Hz) and $^{18}$C NMR (125 MHZ, CDCl$_3$) Data of Molvizarin (2)

| no. | $\delta_H$ | $\delta_c$ | no. | $\delta_H$ | $\delta_c$ |
|---|---|---|---|---|---|
| 15–16 | 1.96–1.62 m | 28.87, 28.30 | 35 | 1.42 d (1.5) | 18.97 |
| 17 | 3.92 m | 82.44 | | | |

Squamotacin (1) was also separated from the other constituents of the extract by multiple open columns followed by normal-phase and reversed-phase HPLC. The respective $^1$H and $^{13}$C NMR signals at δ 3.39, 74.08, 3.85, 83 20, 3.95, 82.52, 3.85, 82.82, 3.93, 82.28, and 3.55, 7136 suggested that 1 contained adjacent THF rings with flanking hydroxyls. The presence of a hydroxyl group at the four position was indicated by the characteristic signals for the Ha and Hb protons at C-3 (Table 3). The relative stereochemistry of threo/trans/threo/trans/erythro was established on the basis of the very close similarities between the $^1$H and $^{13}$C NMR spectra both with respect to the positions and splitting patterns of the resonances. Because of this close relationship, and the unlikely possibility that the ent-isomer is naturally occurring, the absolute stereochemistry of 1 is suggested to be the same as that for 3, whose absolute stereochemistry is known.

TABLE 3a $^{13}$C NMR (125 MHZ, CDCl$_3$) and $^1$H NMR (500 MHZ, CDCl$_3$, J in Hz) Data of squamotacin 1 and bullatacin 3

| | squamotacin (1) | | bullatacin (3) | |
|---|---|---|---|---|
| no. | $\delta_c$ | $\delta_H$ | $\delta_c$ | $\delta_H$ |
| 1 | 174.61 | | 174.58 | |
| 2 | 131.19 | | 131.15 | |
| 3a | 33.35 | 2.40 m | 33.28 | 2.41 m |
| 3b | 33.35 | 2.53 m | 33.28 | 2.53 m |
| 4 | 70.1 | 3.85 m | 69.94 | 3.80 m |
| 5 | 37.39 | 1.45 m | 37.38 | 1.3–2.0 m |
| 6 | 26.05 | 1.36 m | 26.02 | 1.25 m |
| 7–10 | 29.64–29.35 | 1.25 m | 29.66–29.30 | 1.25 m |
| 11 | 25.55 | 1.36 m | 29.66–29.30 | 1.25 m |
| 12 | 33.35 | 1.36 m | 29.66–29.30 | 1.25 m |
| 13 | 74.08 | 3.39 m | 25.54 | 1.25 m |
| 14 | 83.20 | 3.85 m | 33.28 | 1.35 m |
| 15 | 28.35 | 1.63 m | 74.08 | 3.38 m |
| 16 | 28.90 | 1.98 m | 83.25 | 3.83 m |
| 17 | 82.52 | 3.93 m | 28.92 | 1.3–2.0 m |
| 18 | 82.81 | 3.85 m | 26.35 | 1.3–2.0 m |

TABLE 3b $^{13}$C NMR (125 MHZ, CDCl$_3$) and $^1$H NMR (500 MHZ, CDCl$_3$, J in Hz) Data of squamotacin 1 and bullatacin 3

| | squamotacin (1) | | bullatacin (3) | |
|---|---|---|---|---|
| no. | $\delta_c$ | $\delta_H$ | $\delta_c$ | $\delta_H$ |
| 19 | 28.90 | 1.63 m | 82.49 | 3.92 m |
| 20 | 24.51 | 1.98 m | 82.24 | 3.83 m |
| 21 | 82.28 | 3.93 m | 28.92 | 1.3–2.0 m |
| 22 | 71.36 | 3.85 m | 28.35 | 1.3–2.0 m |
| 23 | 32.45 | 1.45 m | 82.77 | 3.92 m |
| 24 | 25.55 | 1.45 m | 71.28 | 3.83 m |

TABLE 3b-continued $^{13}$C NMR (125 MHZ, CDCl$_3$) and $^1$H NMR (500 MHZ, CDCl$_3$, J in Hz) Data of squamotacin 1 and bullatacin 3

| | squamotacin (1) | | bullatacin (3) | |
|---|---|---|---|---|
| no. | $\delta_c$ | $\delta_H$ | $\delta_c$ | $\delta_H$ |
| 25 | 29.64–29.35 | 1.25 m | 32.39 | 1.3–2.0 m |
| 26 | 29.64–29.35 | 1.25 m | 25.54 | 1.25 m |
| 27–31 | 29.64–29.35 | 1.25 m | 29.66–29.30 | 1.25 m |
| 32 | 31.92 | 1.25 m | 31.87 | 1.25 m |
| 33 | 22.68 | 1.25 m | 22.65 | 1.25 m |
| 34 | 14.11 | 0.88 t (7.0) | 14.09 | 0.88 t (7.0) |
| 35 | 151.78 | 7.16 d (1.5) | 151.76 | 7.17 d (1.5) |
| 36 | 77.98 | 5.06 dq (1.5, 6.5) | 77.94 | 5.06 dq (1.5, 7.0) |
| 37 | 19.11 | 1.43 d (1.5) | 19.08 | 1.44 d (1.5) |

The molecular weight of 622 for 1 was assigned on the basis of the MH$^+$ peak at m/z 623 in the CIMS. The EIMS showed fragment peaks at m/z 283 (100) and m/z 335 (80) representing cleavage between C-13 and C-14. On the basis of this information, it was hypothesized that the bis-THF ring system, versus that of 3, was shifted two carbon units toward the lactone ring along the aliphatic chain. The movement of the THF ring units and their flanking hydroxyls from C-15 and C-24 to C-13 and C-22 was confirmed by the EIMS fragmentation pattern of the TMSi derivative FIG. 1). The fragment at m/z 427 was the most intense and indicated major cleavage between C-13 and C-14. Further support was given by the fragment at m/z 271, indicating a cleavage between C-22 and C-23.

EXAMPLE 2

Bioassays

The brine shrimp (*Artemia salina* Leach) test (BST) was performed as modified to determine LC$_{50}$ values in μg/ml. Zhao et al., *Phytochemistry*, 33, p. 1065 (1993). Seven-day in vitro cytotoxicity tests against human tumor cell lines were carried out at the Purdue Cancer Center, using standard protocols for A-549 (human lung carcinoma), MCF-7 (human breast carcinoma) and HT-29 (human colon carcinoma), human renal carcinoma (A-498), human prostate adenocarcinoma (PC-3) and human pancreatic carcinoma (PACA-2) with adriamycin as a positive control. The reported ED$_{50}$ values in μg/ml (Table 1) were tabulated from the same run, except where noted, in order to facilitate comparison for the SAR's.

We claim:

1. A substantially pure compound having the structure

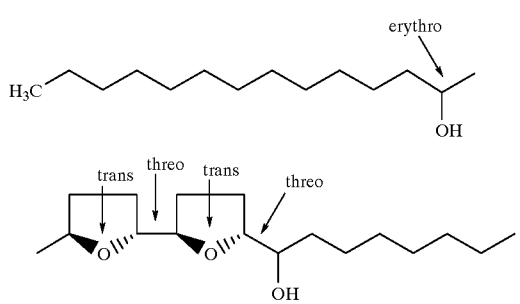

-continued

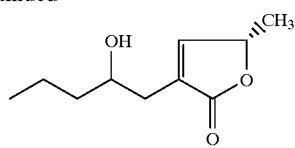

2. An anti-tumor composition comprising an amount of substantially pure squamotacin effective as an anti-tumor agent and a pharmaceutically acceptable carrier therefor.

3. The use of substantially pure squamotacin for the preparation of a pharmaceutical composition for the treatment of a patient having a tumor.

4. The use in accordance with claim 3 wherein the pharmaceutical composition is used for treating a patient having prostate cancer.

5. A method of treating a patient having a tumor, said method comprising administering an effective amount of a pharmaceutical composition comprising squamotacin to a patient afflicted with cancer.

6. A method for treating prostate cancer, said method comprising administering to a patient afflicted with prostate cancer an effective amount of a pharmaceutical composition comprising a substantially pure bioactive compound selected from the group consisting of squamotacin and molvizarin and a pharmaceutically acceptable carrier.

* * * * *